United States Patent [19]

Ungarelli et al.

[11] Patent Number: 5,041,692

[45] Date of Patent: Aug. 20, 1991

[54] PROCESS FOR ALKYLATION OF PHENOLS

[75] Inventors: Raffaele Ungarelli, Novara; Maurizio A. Beretta, Milan, both of Italy

[73] Assignee: Himont Italia S.r.l., Milan, Italy

[21] Appl. No.: 369,248

[22] Filed: Jun. 21, 1989

[30] Foreign Application Priority Data

Jun. 21, 1988 [IT] Italy .............................. 21049 A/88

[51] Int. Cl.$^5$ ....................... C07C 39/14; C07C 39/12
[52] U.S. Cl. ..................................... 568/744; 568/747; 568/780
[58] Field of Search ................ 568/766, 780, 744, 747

[56] References Cited

U.S. PATENT DOCUMENTS

| | | | |
|---|---|---|---|
| 2,394,754 | 2/1946 | D'Alelio | 568/744 |
| 2,432,356 | 12/1947 | Underwood | 568/744 |
| 2,506,410 | 5/1950 | Blake | 568/744 |
| 2,722,556 | 11/1955 | Young et al. | 260/625 |
| 2,832,808 | 4/1958 | Zerbe | 260/625 |
| 4,447,593 | 5/1984 | Funakoshi et al. | 528/176 |
| 4,599,464 | 7/1986 | Dressler | 568/766 |
| 4,661,645 | 4/1985 | Lee et al. | 568/744 |

FOREIGN PATENT DOCUMENTS

| | | | |
|---|---|---|---|
| 0140035 | 8/1983 | Japan | 568/744 |
| 255288 | 4/1970 | U.S.S.R. | 568/744 |

OTHER PUBLICATIONS

Vol. 101 Chem. Abstracts 1984, Abstract No. 210730t, p. 613.
Vol. 100 Chem. Abstracts 1984, Abstract No. 51242, entitled Aralkylhydroquinones, p. 550.
Certified copy of Italian Priority Application No. 21049A/88, filed 6/21/88, also a certified translation.

*Primary Examiner*—Werren B. Lone
*Attorney, Agent, or Firm*—Willian Brinks Olds Hofer Gilson & Lione

[57] ABSTRACT

A process for alkylation of phenols comprising letting a phenol react with a vinyl-aromatic hydrocarbon substituted in the vinyl group, in the presence of an organic solvent and of an acid catalyst in an aqueous solution, and of a polymerization inhibitor.

20 Claims, No Drawings

PROCESS FOR ALKYLATION OF PHENOLS

TECHNICAL FIELD

The present invention relates to a process for alkylation of phenols. More particularly the present invention relates to a process for the alkylation of phenols with vinyl-aromatic hydrocarbons substituted in the vinyl group, which produces high yield and selectively forms a mono-alkylated product.

BACKGROUND ART

Alkylation of phenols with olefins in the presence of acid catalysts is a known process. It is little used in industry however because of low reaction yields. In U.S. Pat. No. 2,832,808 and 2,722,556, for instance, alkylation of phenols is described with olefins in the presence of acid catalysts such as sulphuric acid or phosphoric acid. However, according to these processes, one obtains very low yields, even below 50%, in monoalkylated products or one obtains selectivity to dialkylated products over 90%.

In Japanese Patent Applications 58/140.035 and 59/112.935 the above mentioned drawback is partly overcome. In these applications the preparation of monoalkyl substituted hydroquinone is described by reaction with vinyl aromatic hydrocarbons to obtain reaction yields of the order of 90-93%. However, these processes also are not free from drawbacks, as the alkylation, to have satisfactory results, has to be carried out either by using the reaction product as solvent or by letting the reaction take place in the presence of a poly-substituted hydroquinone.

In U.S. Pat. No. 4,661,645 the synthesis is described of (1-phenylethyl)hydroquinone starting from styrene and hydroquinone in the presence of a Lewis acid and in a homogeneous phase, by using an alkyl ether as homogenisation solvent. In this case the reaction product also contains high quantities of di(phenylethyl)hydroquinone, computable in values over 30% by weight with respect to the mixture of mono and di-substituted products.

The applicant showed in the Italian Patent Application No. 22821 A/87 (filed on Dec. 1, 1987) that drawbacks of the prior art could be overcome by a process for alkylation of phenols, in which the reaction was carried out in a heterogeneous phase. In said application a process is described for alkylation of phenols comprising letting a phenol react with a vinyl-aromatic hydrocarbon in the presence of an organic solvent and of a catalyst which is an inorganic acid diluted in water. According to the process of the above mentioned application one can obtain a yield in monoalkylated product over 95% and a selectivity to dialkylated products below 5%, with a purity relating to mono and di-alkylated products over 99.9%. However, if use is made for the alkylation of a vinyl-aromatic hydrocarbon substituted in the vinyl group with an alkyl radical, such as for instance alpha-methyl-styrene, the alkylation yields, calculated on olefin, are low because those hydrocarbons are very reactive and tend to give oligomers like the following:

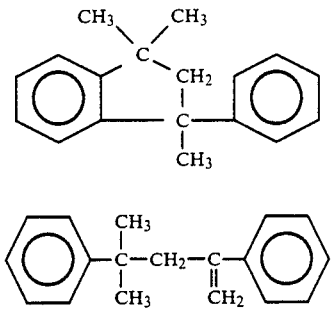

DISCLOSURE OF THE INVENTION

Applicants have now found that, if a vinyl-aromatic hydrocarbon substituted in the vinyl group is used for the alkylation, the alkylation yield can be considerably increased, either by addition to the reaction medium, or by causing the formation in situ, of a polymerization inhibitor which is effective in preventing the initial formation of the first part of an oligomeric chain, such as dimers, trimers and so on.

Therefore the object of the present invention is a process for alkylation of phenols comprising letting a phenol react with a vinyl-aromatic hydrocarbon, having one or more alkyl substituents in the vinyl groups, in the presence of an organic solvent, and in the presence of a catalyst which is an inorganic acid in an aqueous solution and in the presence of an inhibitor of polymerization or oligomerization.

Examples of phenols which can be used in the process object of the present invention are hydroquinone, resorcinol, pyrocatechol, pyrogallol, benzophenol, cresols, p-octyl phenol, dihydroxydiphenyl, alpha-naphthol, beta-naphthol and the like; hydroquinone is the particularly preferred reactant.

The vinyl aromatic hydrocarbon is selected from among those having the general formula:

   (1)

wherein Ar represents an aryl group containing 6-18 carbon atoms, and wherein $R_1$, $R_2$, $R_3$ are selected from hydrogen and alkyl radicals having 1-10 carbon atoms, but at least one of $R_1$, $R_2$ and $R_3$ is an alkyl radical.

Examples of products having general formula (1) are alpha-methyl styrene, alpha-ethyl styrene, p-methyl-alpha-methyl styrene, beta-methyl styrene and the like. A particularly preferred product is alpha-methyl styrene.

The following compounds are efficient inhibitors: acetone or its derivatives, such as diacetone alcohol or mesityl oxide. Inhibitors may be either added to the system or formed in situ or recycled from a preceding test or run. Other inhibitors include p-quinone, 2-6-diterbutyl p-cresol (or BHT), p-nitrophenol, p-aminophenol, nitrobenzene and although less efficient, inorganic or organic salts, and oxides of metals, for instance of $Cu^{++}$ (such as $CuCl_2$, CuSO 4, $Cu(CH_3COO)_2$ and the like).

DETAILED DESCRIPTION OF THE INVENTION

According to a preferred embodiment of the present invention, a phenol is reacted in a slight molar excess with respect to the aromatic hydrocarbon; molar ratios of phenol/vinyl-aromatic hydrocarbon ranging from 0.5 to 5, preferably from 1 to 2, are used with the greatest advantage.

The alkylation reaction is carried out in a solvent selected from the ones having a boiling temperature compatible with the reaction temperature and a good solubility chiefly as to the final product. Aromatic hydrocarbons such as toluene, xylenes and the like, have proved to be suitable solvents. The solvent can be used in any ratio by weight with respect to phenol, however ratios by weight solvent/phenol ranging from 0.5 to 5 and preferably from 1 to 2.5 are most commonly used.

Any inorganic acid can be used as catalyst of the alkylation process of the present invention. Orthophosphoric acid, pyrophosphoric acid and sulphuric acid, diluted in water at 60–90% by weight and preferably at 70–80% are, however, the preferred ones.

The catalyst is used with molar ratios with, respect to the phenol, ranging from 1 to 10, and preferably from 3 to 5.

The inhibitor is employed in the system with molar ratios ranging from 0.01 to 5, preferably from 0.05 to 1, with respect to vinyl aromatic hydrocarbon.

The alkylation reaction of the process of the present invention is carried out at room, or atmospheric, pressure and at a temperature ranging from 90 to 120° C, preferably from 110° to 115° C. When the alkylation reaction is over, the organic phase consisting of the solvent and of the raw product coming from the reaction, is separated by decantation from the catalytic system and the product is recovered by crystallization from the solvent.

The process of the present invention proved to be very convenient for preparing particular phenols, prevailingly monoalkylated phenols, which can be used, on account of their high degree of purity as monomers for the production of thermotropic liquid crystalline polymers. An example is (alpha-phenylisopropyl)hydroquinone. The purity of the alkylated phenol is already very high at the first crystallization. They can however be further easily purified by crystallization from mixture of solvents of industrial use (for instance toluene/hexane or xylene/hexane).

Inhibiting the formation of the previously mentioned oligomers, considerably lowers the manufacturing costs of the monoalkylated product. This is because of a yield increase of about 50%, and on account of the simplification, and consequent lower cost, for recovering the product by crystallization, as the oligomers (oily products) act as solvents of the alkylated products.

A few examples will be given hereinafter by way of illustration but not of limitation, in order to better understand the present invention and to carry out the same.

EXAMPLE 1

Comparison Example 22 g (0.2 moles) of hydroquinone, ml 50 of xylene, 131 g of $H_3PO_4$ (as an aqueous solution of 75% by weight) were loaded into a 250 ml glass reactor equipped with a stirrer, thermometer, reflux cooler, dropping funnel and outside heating bath. The mixture was heated to 113° C. and alpha-methylstyrene was added in amount equal to 23.6 g (0.2 moles). After 7 hours at 115° C. under stirring the two phases were allowed to stratify followed by a removing of the solution of $H_3PO_4$ and then a rinsing of the xylenic solution with $NaHCO_3$, in an aqueous solution at 5% by weight, and with water.

The organic solution was diluted with ml 100 of n-hexane under stirring, and cooled to 20° C. to complete the crystallization of (alpha-phenylisopropyl)hydroquinone. The product was filtered, followed by rinsing with 20 ml of n-hexane.

After drying 18 g of a pulverulent yellowish product was obtained containing, by gas-chromatography (GC), 98.8% of (alpha-phenylisopropyl)hydroquinone, equal to 0.978 moles, and 0.8% of 2.5-bis(alpha-phenylisopropyl)hydroquinone, equal to 0.0004 moles.

By evaporating the mother liquor, or waters from filtration until a constant weight, 12.8 g of a viscous brown product was obtained containing 10.2% (GC) of monosubstituted hydroquinone, equal to 0.0057 moles, 1.5% (GC) of disubstituted hydroquinone, equal to 0.00055 moles and 88.3% (GC) of oligomers of methylstyrene.

Total molar yield (alpha-phenylisopropyl)hydroquinone/alpha-methyletryene=41.85%, molar yield of alkylation, mono and disubstituted hydroquinone/alpha-methylstryene,=42.8%.

EXAMPLE 2

The procedure of Example 1 was followed while adding 2.9 g of acetone to xylene. One obtained 26.4 g of a dry crystallized product having a purity, or titre (GC), of 98.9% of (alpha-phenylisopropyl)hydroquinone and 1.05% of 2.5-bis(alpha-phenylisopropyl)hydroquinone; the mother-waters coming from filtration, after having been evaporated until a constant weight, gave a residue of 12.4 g having a titre (GC)=2.9% and 4.1% in mono and disubstituted hydroquinone respectively. Total molar yield (alpha-phenylisopropyl)hydroquinone/alpha-methylstryene=58%; molar yield of alkylation=59.13%.

EXAMPLE 3

One follows the procedure of Example 1, while adding to xylene 12.4 g of residue obtained by evaporation of the mother-waters coming from the filtration according to Example 2.

After crystallization and drying 28.8 g of a solid was obtained having titre (GC) 98.7% of (alpha-phenylisopropyl)hydroquinone and 1.2% of 2,5-bis (alpha-phenylisopropyl)hydroquinone.

EXAMPLES 4-11

One follows the procedure of Example 2, while replacing acetone with other polymerization inhibitors as indicated in Table I. Table I summarizes results obtained including the ones of Examples 1–3. By reaction of hydroquinone with alpha-methyl styrene (indicated in the Table by MST) one obtained essentially the pure compound:

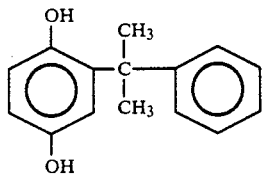

which is usually defined as mono-methylstyrylhydroquinone (MSHQ). The corresponding dialkylated compound, obtained in much lower amount, is usually defined as di-methylstyrylhydroquinone (DMSHQ). In the Table "m.w." means "mother-water".

TABLE I

| Example No | Hydroquinone g. | α-methyl styrene g. | $H_3PO_4$ Sol. 75% g. | Xylene ml | Inhibitor Type | g. | Temp. °C. | Time hours |
|---|---|---|---|---|---|---|---|---|
| 1 | 22 | 23.6 | 131 | 50 | — | — | 113 | 7 |
| 2 | 22 | 23.6 | 131 | 50 | Acetone | 2.9 | 112–113 | 7 |
| 3 | 22 | 23.6 | 131 | 50 | m.w. residue Test 2 | 12.4 | 113 | 7 |
| 4 | 44 | 47.2 | 262 | 75 | p-quinone | 1.3 | 115 | 6.5 |
| 5 | 44 | 47.2 | 327 | 100 | 2-6diterbutyl paracresol | 2.6 | 115 | 7.5 |
| 6 | 33 | 23.6 | 262 | 50 | p-nitrophenol | 0.8 | 115 | 8 |
| 7 | 22 | 23.6 | 131 | 25 | p-aminophenol | 0.6 | 114 | 7 |
| 8 | 22 | 23.6 | 131 | 50 | $CuCl_2.2H_2O$ | 1 | 116 | 8 |
| 9 | 110 | 94.4 | 550 | 150 | Diacetone alcohol | 15 | 111–115 | 8 |
| 10 | 110 | 118 | 655 | 250 | mesityl oxide | 15 | 111–116 | 7 |
| 11 | 22 | 23.6 | 131 | 50 | Nitrobenzene | 12.3 | 115 | 7 |

| | PRODUCT | | | | | | |
|---|---|---|---|---|---|---|---|
| | crystallized | | m.w. residue | | | molar yield % | |
| Example No | g. | MSHQ % | DMSHQ % | g. | MSHQ % | DMSHQ % | $\frac{MSHQ}{MST}$ | $\frac{MSHQ + DMSHQ}{MST}$ |
| 1 | 18 | 98.8 | 0.8 | 12.8 | 10.2 | 1.5 | 41.85 | 42.8 |
| 2 | 26.4 | 98.9 | 1.05 | 12.4 | 2.9 | 4.1 | 58 | 59.13 |
| 3 | 28.8 | 98.7 | 1.2 | 22.4 | 3.1 | 3.9 | 63.8 | 67.32 |
| 4 | 51.7 | 99 | 0.9 | 23.2 | 3.3 | 2.9 | 56.91 | 58.54 |
| 5 | 50.9 | 99.4 | 0.4 | 26.8 | 3.5 | 2.4 | 56.46 | 57.67 |
| 6 | 24.2 | 98.9 | 1 | 12.6 | 3.6 | 2.8 | 53.43 | 55.17 |
| 7 | 24.1 | 99 | 0.8 | 12.4 | 3.4 | 3.3 | 53.20 | 54.94 |
| 8 | 21.6 | 99.1 | 0.8 | 11.9 | 5.4 | 4.6 | 48.31 | 50.38 |
| 9 | 106.5 | 98.8 | 1.1 | 50 | 3.1 | 4.3 | 58.49 | 60.89 |
| 10 | 125 | 98.9 | 0.9 | 60.2 | 4.3 | 3.9 | 55.31 | 57.32 |
| 11 | 25.5 | 98.8 | 1.1 | 12.3 | 3.5 | 4.2 | 56.2 | 57 |

We claim:

1. A process for alkylation of phenols comprising reacting a phenol with a vinyl-aromatic hydrocarbon having one or more alkyl substituents in the vinyl group, in the presence of an organic solvent and an aqueous solution of an inorganic acid catalyst and an inhibitor of the polymerization reaction of the vinyl-aromatic hydrocarbon and wherein the catalyst is orthophosphoric acid, pyrophosphoric acid or sulphuric acid, diluted in water to 60–90% by weight, and wherein the solvent is an aromatic hydrocarbon and wherein the inhibitor of polymerization is acetone or acetone derivatives or p-quinone or 2-6-diterbutyl p-cresol or p-nitrophenol or p-aminophenol or nitrobenzene or inorganic or organic acids of metals or metal oxides.

2. A process according to claim 1, wherein the phenol is selected from the group consisting of hydroquinone, resorcinol, pyrocatechol, pyrogallol, benzophenol, cresols, p-octyl phenol, dihydroxydiphenyl, alpha-naphthol, beta-naphthol.

3. A process according to claim 1 wherein the vinyl-aromatic hydrocarbon is selected among the ones having general formula:

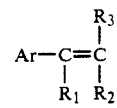

wherein Ar represents an aryl group containing from 6 to 18 carbon atoms, whereas $R_1$, $R_2$ and $R_3$ are selected among hydrogen and alkyl radicals having from 1 to 10 carbon atoms, but at least one of $R_1$, $R_2$ or $R_3$ is an alkyl radical.

4. A process according to claim 3, wherein the vinyl-aromatic hydrocarbons substituted in the vinyl group are alpha-methyl styrene, alpha-ethyl styrene, p-methyl-alpha-methyl styrene, or beta-methyl styrene.

5. A process according to claim 1, wherein the molar ratio phenol/vinyl aromatic hydrocarbon ranges from 0.5 to 5.

6. A process according to claim 1, wherein the ratio by weight solvent/phenol ranges from 1 to 10.

7. A process according to claim 1, wherein the molar ratio catalyst/phenol ranges from 1 to 10.

8. A process according to claim 1, wherein the molar ratio inhibitor of polymerization/vinyl-aromatic hydrocarbon ranges from 0.01 to 5.

9. A process according to claim 1, wherein the reaction temperature ranges from 90 to 120° C.

10. The process of claim 1, wherein said inhibitor is a salt or oxide of copper.

11. The process of claim 1 wherein said inhibitor is acetone or an acetone derivative.

12. The process of claim 1 wherein said inhibitor is p-quinone.

13. The process of claim 1 wherein said inhibitor is 2-6-diterbutyl p-cresol.

14. The process of claim 1 wherein said inhibitor is p-nitrophenol.

15. The process of claim 1 wherein said inhibitor is p-aminophenol.

16. The process of claim 1 wherein said inhibitor is nitrobenzene.

17. The process of claim 1 wherein said inhibitor is an inorganic or organic salt of a metal.

18. The process of claim 1 wherein said inhibitor is a metal oxide.

19. The process of claim 1 wherein said inhibitor is $CuCl_2$, $CuSO_4$, $Cu(CH_3COO)_2$.

20. The process of claim 1 wherein said solvent is toluene or xylene.

* * * * *

UNITED STATES PATENT AND TRADEMARK OFFICE
CERTIFICATE OF CORRECTION

PATENT NO. : 5,041,692

DATED : August 20, 1991

INVENTOR(S) : Raffaele Ungarelli, Maurizio A. Beretta & L. Lawrence Chapoy

It is certified that error appears in the above-identified patent and that said Letters Patent is hereby corrected as shown below:

On the title page, in element [75] after Itally,
add --and L. Lawrence Chapoy of Novara, Italy--.

Signed and Sealed this

Third Day of November, 1992

*Attest:*

DOUGLAS B. COMER

*Attesting Officer*    Acting Commissioner of Patents and Trademarks